United States Patent
Watakabe et al.

(10) Patent No.: US 8,933,264 B2
(45) Date of Patent: Jan. 13, 2015

(54) METHOD FOR PRODUCING ORGANIC COMPOUND HAVING SULFO GROUP, METHOD FOR PRODUCING LIQUID COMPOSITION, AND METHOD FOR HYDROLYZING ORGANIC COMPOUND HAVING FLUOROSULFONYL GROUP

(71) Applicant: Asahi Glass Company, Limited, Chiyoda-ku (JP)

(72) Inventors: Atsushi Watakabe, Tokyo (JP); Yoshitomi Morizawa, Tokyo (JP); Hisao Hori, Tokyo (JP); Takehiko Sakamoto, Tokyo (JP); Tomoyuki Fujita, Tokyo (JP); Kana Ishikawa, Tokyo (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 0 days.

(21) Appl. No.: 14/190,383

(22) Filed: Feb. 26, 2014

(65) Prior Publication Data
US 2014/0179948 A1    Jun. 26, 2014

Related U.S. Application Data

(63) Continuation of application No. PCT/JP2012/071872, filed on Aug. 29, 2012.

(51) Int. Cl.
| | | |
|---|---|---|
| C07C 309/00 | (2006.01) | |
| C08F 114/26 | (2006.01) | |
| C07B 45/02 | (2006.01) | |
| C08F 8/12 | (2006.01) | |
| C08J 11/14 | (2006.01) | |
| C07C 303/22 | (2006.01) | |

(52) U.S. Cl.
CPC .............. *C08F 114/26* (2013.01); *C07B 45/02* (2013.01); *C08F 8/12* (2013.01); *C08J 11/14* (2013.01); *C07C 303/22* (2013.01); *C08J 2327/12* (2013.01)
USPC ........................................................ 562/101

(58) Field of Classification Search
None
See application file for complete search history.

(56) References Cited

FOREIGN PATENT DOCUMENTS

| | | |
|---|---|---|
| JP | 2000-86809 | 3/2000 |
| JP | 2002-260705 | 9/2002 |
| JP | 2002-332272 | 11/2002 |
| JP | 2004-196994 | 7/2004 |
| JP | 2005-82749 | 3/2005 |
| JP | 2010-27519 | 2/2010 |
| JP | 2010-257765 | 11/2010 |
| JP | 2011-111502 | 6/2011 |

OTHER PUBLICATIONS

International Search Report issued Oct. 23, 2012 in PCT/JP2012/071872 filed Aug. 29, 2012.
T. Gramstad, R.N. Haszeldine, Journal of the Chemical Society (1957), p. 2640-2645.

*Primary Examiner* — Karl J Puttlitz
(74) *Attorney, Agent, or Firm* — Oblon, Spivak, McClelland, Maier & Neustadt, L.L.P.

(57) ABSTRACT

To provide a method for producing an organic compound having a sulfo group by efficiently hydrolyzing an organic compound having a fluorosulfonyl group with a small number of steps with a small quantity of waste liquid.

A method for producing an organic compound having a sulfo group, which comprises bringing an organic compound having a fluorosulfonyl group into contact with subcritical water at from 200 to 320° C. to convert the fluorosulfonyl group into a sulfo group.

10 Claims, 4 Drawing Sheets

METHOD FOR PRODUCING ORGANIC COMPOUND HAVING SULFO GROUP, METHOD FOR PRODUCING LIQUID COMPOSITION, AND METHOD FOR HYDROLYZING ORGANIC COMPOUND HAVING FLUOROSULFONYL GROUP

TECHNICAL FIELD

The present invention relates to a method for producing an organic compound having a sulfo group, a method for producing a liquid composition containing an organic compound having a sulfo group, and a method for hydrolyzing an organic compound having a fluorosulfonyl group.

BACKGROUND ART

As an organic compound having a sulfo group ($—SO_3H$), a fluorinated polymer having sulfo groups, and a fluorinated organic compound having a sulfo group excluding a fluorinated polymer have been known.

A fluorinated polymer having sulfo groups and its derivative are used e.g. as an electrolyte membrane of a polymer electrolyte fuel cell or an ion exchange resin covering catalyst fine particles (such as metal-supported carbon black) in a catalyst layer of a polymer electrolyte fuel cell. Further, a fluorinated polymer having sulfo groups and its derivative are used as a liquid composition as dispersed or dissolved in a medium containing water. Such a liquid composition is used as a material to form an electrolyte membrane or a catalyst layer of a polymer electrolyte fuel cell.

A fluorinated organic compound having a sulfo group excluding a fluorinated polymer is used e.g. as an electrolytic solution of a lithium ion battery or an additive for the electrolytic solution after conversion into a lithium salt.

As a method for producing an organic compound having a sulfo group, for example, the following method has been proposed.

(1) A method comprising a step of subjecting a compound having a fluorosulfonyl group ($—SO_2F$) to alkali hydrolysis treatment in an alkali solution containing an organic solvent and water to convert the fluorosulfonyl group to a sulfonate type functional group ($—SO_3M$, wherein M is an alkali metal), and a step of subjecting the compound having the sulfonate type functional group to acid treatment to convert the sulfonate type functional group into a sulfo group (Patent Documents 1 to 3, Non-Patent Document 1).

As a method for producing a liquid composition, for example, the following method has been proposed.

(2) A method of heating a fluorinated polymer having sulfo groups or its derivative in a medium, with stirring and mixing (Patent Document 3).

PRIOR ART DOCUMENTS

Patent Documents

Patent Document 1: JP-A-2005-082749
Patent Document 2: JP-A-2004-196994
Patent Document 3: JP-A-2002-260705

Non-Patent Document

Non-Patent Document 1: T. Gramstad, R. N. Haszeldine, Journal of the Chemical Society (1957), p. 2640-2645.

DISCLOSURE OF INVENTION

Technical Problem

In a case where an organic compound having a sulfo group is to be produced by the method (1), in the case of the production methods disclosed in Patent Documents 1 to 3, in the step of alkali hydrolysis treatment, in the step of acid treatment and by washing with water repeatedly carried out after the respective steps, a large quantity of waste liquid will form. Further, the production cost tends to be high due to a large number of steps and a large quantity of waste liquid. The production method disclosed in Non-Patent Document 1 involves distillation in the step of acid treatment. The production cost tends to be high due to many steps.

In a case where a liquid composition is to be produced by the method (2), the fluorinated polymer having sulfo groups or its derivative obtained by the method (1) should be isolated in advance, and stirring and mixing will take long, such being inefficient.

It is an object of the present invention to provide a method for efficiently producing an organic compound having a sulfo group with a small number of steps with a small quantity of waste liquid.

It is an object of the present invention to provide a method for efficiently producing a liquid composition containing an organic compound having a sulfo group and water with a small number of steps with a small quantity of waste liquid.

It is an object of the present invention to provide a method for efficiently hydrolyzing an organic compound having a fluorosulfonyl group with a small number of steps with a small quantity of waste liquid.

Solution to Problem

The present invention provides the following method [1] to [3] for producing an organic compound having a sulfo group, a method [4] to [6] for producing a liquid composition and a method [7] to [10] for hydrolyzing an organic compound having a fluorosulfonyl group.

[1] A method for producing an organic compound having a sulfo group, which comprises bringing an organic compound having a fluorosulfonyl group into contact with subcritical water at from 200 to 320° C. to convert the fluorosulfonyl group into a sulfo group.

[2] The method for producing an organic compound having a sulfo group according to [1], wherein the organic compound having a fluorosulfonyl group is a perfluorocompound.

[3] The method for producing an organic compound having a sulfo group according to [1] or [2], wherein the organic compound having a fluorosulfonyl group is a fluorinated polymer.

[4] A method for producing a liquid composition containing an organic compound having a sulfo group and water, which comprises treating a composition containing an organic compound having a fluorosulfonyl group and water at from 200 to 320° C. under conditions that water becomes subcritical water, to convert the fluorosulfonyl group into a sulfo group to obtain a composition containing an organic compound having a sulfo group and water.

[5] The method for producing a liquid composition according to [4], wherein the organic compound having a fluorosulfonyl group is a perfluorocompound.

[6] The method for producing a liquid composition according to [4] or [5], wherein the organic compound having a fluorosulfonyl group is a fluorinated polymer.

[7] A method for hydrolyzing an organic compound having a fluorosulfonyl group, which comprises bringing an organic compound having a fluorosulfonyl group into contact with subcritical water at from 200 to 320° C. to hydrolyze the fluorosulfonyl group.

[8] The method for hydrolyzing an organic compound having a fluorosulfonyl group according to [7], wherein the organic compound having a fluorosulfonyl group is a perfluorocompound.

[9] The method for hydrolyzing an organic compound having a fluorosulfonyl group according to [7] or [8], wherein the organic compound having a fluorosulfonyl group is a fluorinated polymer.

[10] The method for hydrolyzing an organic compound having a fluorosulfonyl group according to any one of [7] to [9], wherein the fluorosulfonyl group is converted into a sulfo group by hydrolysis.

Advantageous Effects of Invention

According to the method for producing an organic compound having a sulfo group of the present invention, an organic compound having a sulfo group can be produced efficiently with a small number of steps with a small quantity of waste liquid.

According to the method for producing a liquid composition of the present invention, a liquid composition containing an organic compound having a sulfo group and water can be produced efficiently with a small number of steps with a small quantity of waste liquid.

According to the method for hydrolyzing an organic compound having a fluorosulfonyl group of the present invention, an organic compound having a fluorosulfonyl group can be hydrolyzed efficiently with a small number of steps with a small quantity of waste liquid.

DESCRIPTION OF EMBODIMENTS

Figure 1:
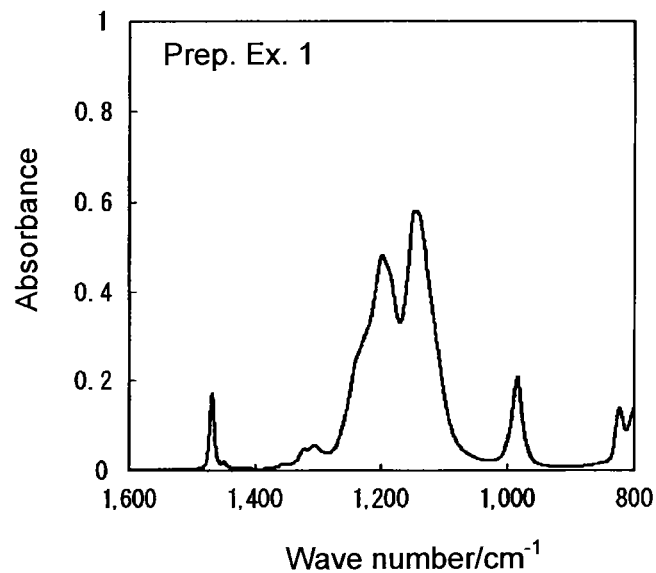
FIG. 1 is an infrared absorption spectrum of perfluoropolymer (1) in Preparation Example 1.

"Subcritical water" in this specification means water in a liquid state at a temperature of at least 100° C. and less than the critical temperature.

"Fluorinated organic compound" in this specification means an organic compound having at least one fluorine atom in its molecule.

"Fluorinated polymer" in this specification means a polymer having at least one fluorine atom in its molecule.

"Perfluorocompound" in this specification means an organic compound in which all the hydrogen atoms bonded to a carbon atom are substituted by fluorine atoms.

"Perfluoropolymer" in this specification means a polymer obtained by polymerizing only a perfluoromonomer in which all the hydrogen atoms bonded to a carbon atom are substituted by fluorine atoms. The perfluoropolymer may have hydrogen atoms bonded to a carbon atom, derived from a polymerization initiator or a chain transfer agent.

"Unit" in this specification means a unit derived from a monomer, formed by polymerization of the monomer. The unit may be a unit formed directly by the polymerization reaction, or may be a unit having a part of such a unit converted into another structure by treating the polymer.

"Monomer" in this specification means a compound having a polymerizable carbon-carbon double bond.

[Method for Producing Organic Compound Having Sulfo Group]

The method for producing an organic compound having a sulfo group of the present invention is a method for producing an organic compound having a sulfo group, by bringing a compound having a fluorosulfonyl group into contact with subcritical water at from 200 to 320° C. to convert the fluorosulfonyl group in the organic compound having a fluorosulfonyl group into a sulfo group.

The proportion of the fluorosulfonyl group converted to a sulfo group in the fluorosulfonyl group (100 mol %) in the organic compound having a fluorosulfonyl group is preferably at least 50 mol %, more preferably at least 70 mol %, further preferably at least 80 mol %, particularly preferably at least 90 mol %.

(Organic Compound having Fluorosulfonyl Group)

The organic compound having a fluorosulfonyl group may, for example, be a polymer having fluorosulfonyl groups or an organic compound having a fluorosulfonyl group excluding a polymer.

The organic compound having a fluorosulfonyl group excluding a polymer may be an organic compound having a fluorosulfonyl group and having no aromatic ring or an organic compound having a fluorosulfonyl group and having an aromatic ring, and in view of the heat resistance, preferred is an organic compound having a fluorosulfonyl group and having an aromatic ring.

The organic compound having a fluorosulfonyl group excluding a polymer is preferably a fluorinated organic compound, particularly preferably a perfluorocompound, in view of the heat resistance. The perfluorocompound may, for example, be $CF_3(CF_2)_jSO_2F$ (wherein j is an integer of from 1 to 12) or $FSO_2(CF_2)_kSO_2F$ (wherein k is an integer of from 2 to 4).

The polymer having fluorosulfonyl groups is preferably a fluorinated polymer containing a fluorine atom bonded to a carbon atom in the units derived from a monomer, particularly preferably a perfluoropolymer, in view of the heat resistance.

The fluorinated polymer containing a fluorine atom bonded to a carbon atom in the units derived from a monomer may be a copolymer having units derived from a monomer (m1) having a fluorosulfonyl group and units derived from a monomer (m2) having no fluorosulfonyl group, either one of or both units containing a fluorine atom bonded to a carbon atom.

The monomer (m1) having a fluorosulfonyl group is preferably a perfluoromonomer in view of the heat resistance of a polymer to be obtained. The perfluoromonomer having a fluorosulfonyl group may be a monomer represented by the following formula (m1-1) to (m1-8):

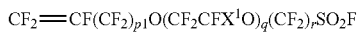 (m1-1)

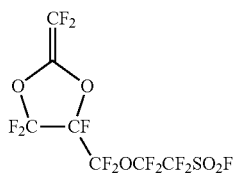 (m1-2)

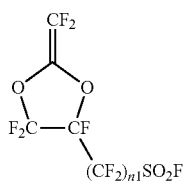 (m1-3)

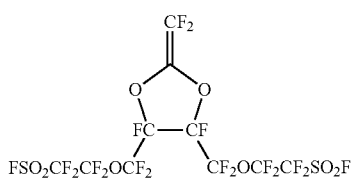 (m1-4)

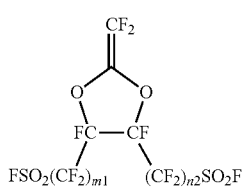 (m1-5)

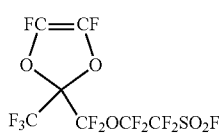 (m1-6)

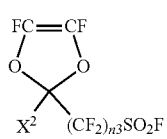 (m1-7)

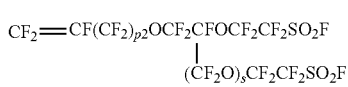 (m1-8)

In the above formulae, each of $X^1$ and $X^2$ is a fluorine atom or a trifluoromethyl group, each of p1 and p2 is 0 or 1, q is an integer of from 0 to 2, r is an integer of from 1 to 12, s is 0 or 1, each of n1 to n3 is an integer of from 1 to 6, and m1 is an integer of from 1 to 6.

As the monomer (m1-1), the following monomers are preferred in view of availability or easy preparation.

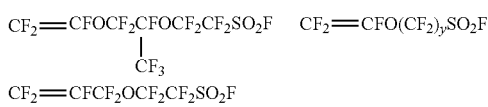

In the above formula, y is 2 or 4.

As the monomer (m2) having no fluorosulfonyl group, the following monomers may be mentioned.

Fluoroethylenes: $CF_2=CF_2$, $CF_2=CFCl$, $CF_2=CFH$, $CFH=CH_2$, $CF_2=CH_2$, etc.

Fluoropropylenes: $CF_2=CFCF_3$, $CF_2=CHCF_3$, $CH_2=CHCF_3$, $CH_2=CFCF_3$, etc.

Polyfluoroalkylethylenes having a $C_{2-12}$ fluoroalkyl group: $CF_3CF_2CH=CH_2$, $CF_3CF_2CF_2CF_2CH=CH_2$, $CF_3CF_2CF_2CF_2CF=CH_2$, $CF_2HCF_2CF_2CF=CH_2$, etc.

Perfluorovinyl ethers: $R^f(OCFX^3CF_2)_tOCF=CF_2$ (wherein $R^f$ is a $C_{1-6}$ perfluoroalkyl group, $X^3$ is a fluorine atom or a trifluoromethyl group, and t is an integer of from 0 to 5), $CF_2=CFCF_2OCF=CF_2$, $CF_2=CF(CF_2)_2OCF=CF_2$, etc.

Perfluorovinyl ethers having a carboxylic acid type functional group: $YCF_2CF_2CF_2OCF=CF_2$ (wherein Y is a carboxylic acid type functional group), etc.

Hydrocarbon monomers: ethylene, propylene, isobutene, 1-butene, etc.

Monomers having a cyclic structure: a monomer having a 1,3-dioxolane structure, a monomer having a 1,3-dioxole structure, etc.

Here, the carboxylic acid type functional group means a carboxy group (—COOH) or a functional group capable of being converted into a carboxy group by hydrolysis or neutralization. The functional group capable of being converted into a carboxy group may, for example, be —CN, —COF, —COOR$^1$ (wherein R$^1$ is a $C_{1-10}$ alkyl group), —COOM$^1$ (wherein M$^1$ is an alkali metal or a quaternary ammonium salt group) or —CONR$^2$R$^3$ (wherein each of R$^2$ and R$^3$ which may be the same or different, is a hydrogen atom or a $C_{1-10}$ alkyl group).

In this specification, a perfluorovinyl ether having a carboxylic acid type functional group will be called a perfluoromonomer, since even if a functional group capable of being converted into a carboxy group has a hydrogen atom bonded to a carbon atom, the hydrogen atom is removed by conversion into a carboxy group.

The monomer (m2) having no fluorosulfonyl group is preferably a perfluoromonomer in view of the heat resistance of a polymer to be obtained. As the perfluoromonomer having no fluorosulfonyl group, the following monomers may be mentioned.

 (m2-1)

 (m2-2)

 (m2-3)

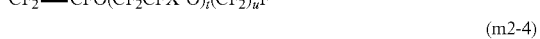 (m2-4)

 (m2-5)

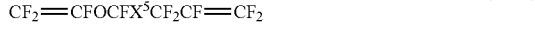 (m2-6)

 (m2-7)

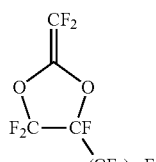

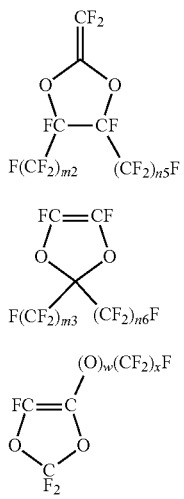

In the above formulae, each of $X^4$ and $X^5$ is a fluorine atom or a trifluoromethyl group, t is an integer of from 0 to 3, u is an integer of from 1 to 12, v is an integer of from 1 to 6, each of n4 to n6 is an integer of from 1 to 6, each of m2 and m3 is an integer of from 1 to 6, w is 0 or 1, and x is an integer of from 1 to 3.

The combination of the monomer (m1) having a fluorosulfonyl group and the monomer (m2) having no fluorosulfonyl group is preferably a combination of the monomer (m1-1) and the monomer (m2-1), a combination of the monomer (m1-8) and the monomer (m2-1), a combination of the monomer (m1-2) and the monomer (m2-1), a combination of the monomer (m1-1), the monomer (m1-8) and the monomer (m2-1), or a combination of the monomer (m1-8), the monomer (m2-1) and the monomer (m2-3) in view of usefulness as a polymer for a polymer electrolyte fuel cell and easy production.

The molecular weight of the organic compound having a fluorosulfonyl group in the present invention is not particularly limited. In the case of a fluorinated polymer having fluorosulfonyl groups, $T_Q$ which is an index of the molecular weight is preferably at least 150° C., more preferably from 180 to 350° C., particularly preferably from 200 to 300° C., in view of usefulness of an obtainable fluorinated polymer having sulfo groups as an ion exchange resin. $T_Q$ is a temperature (unit: ° C.) at which the volume flow rate is 100 mm³/sec. The volume flow rate is the flow rate represented by the unit mm³/sec when a polymer is melted and extruded from an orifice having a length of 1 mm and an inner diameter of 1 mm under an elevated pressure of 2.94 MPa. Usually, the higher the $T_Q$, the higher the molecular weight.

Further, the mass average molecular weight (Mw) of the fluorinated polymer having fluorosulfonyl groups is preferably from 1,000 to 1,000,000, particularly preferably from 5,000 to 1,000,000.

The content of the fluorosulfonyl groups in the fluorinated polymer having fluorosulfonyl groups is preferably from 0.5 to 3 mmol/g, more preferably from 0.7 to 2.5 mmol/g, particularly preferably from 1.0 to 2.2 mmol/g, in view of usefulness of an obtainable fluorinated polymer having sulfo groups as an ion exchange resin particularly as a proton exchange resin. When the content of the fluorosulfonyl groups is at least the lower limit value of the above range, the ion conductivity particularly the proton conductivity of an obtainable fluorinated polymer having sulfo groups tends to be high, and such a polymer is highly useful as an ion exchange resin. When the content of the fluorosulfonyl groups is at most the upper limit value of the above range, an obtainable fluorinated polymer having sulfo groups will not swell too much by water or a protic solvent, and the strength of the polymer tends to be favorable.

The content of the fluorosulfonyl groups can be obtained by dipping and hydrolyzing the fluorinated polymer having fluorosulfonyl groups in a sodium hydroxide solution containing water and methanol as a solvent, and subjecting the obtained solution to back titration with diluted hydrochloric acid.

The shape of the fluorinated polymer having fluorosulfonyl groups is not particularly limited. It may, for example, be a form of a powder, pellets, a formed product (a film or strands) or the like.

The organic compound(s) having a fluorosulfonyl group may be one compound, or a mixture of two or more compounds.

The organic compound having a fluorosulfonyl group may be in a state of a composition with another material or in a state where it covers another material. Specifically, a composition with an inorganic material (such as carbon or silica), a composition with an organic compound having no fluorosulfonyl group, a coating on another material (such as paper, fibers or a plastic), or a dispersion in water and/or an organic solvent.

The content of the organic compound having a fluorosulfonyl group is preferably from 0.1 to 100 parts by mass, more preferably from 1 to 70 parts by mass, particularly preferably from 3 to 45 parts by mass per 100 parts by mass of water.

The reaction of converting a fluorosulfonyl group into a sulfo group in the present invention is a reaction of bringing an organic compound having a fluorosulfonyl group into contact with subcritical water under pressure and temperature conditions that water in the reaction system becomes subcritical water, to convert the fluorosulfonyl group into a sulfo group. This reaction is basically one type of hydrolysis.

The temperature of the reaction system is at least 200° C., preferably at least 240° C., particularly preferably at least 260° C. When the temperature of the reaction system is at least the lower limit value, the rate of the conversion reaction of a fluorosulfonyl group into a sulfo group tends to be good.

The temperature of the reaction system is at most 320° C., preferably at most 300° C., particularly preferably at most 290° C. When the temperature of the reaction system is at most the upper limit value, the organic compound having a fluorosulfonyl group is less likely to undergo a decomposition reaction other than the above reaction.

The temperature of the reaction system is within a range of from 200 to 320° C., preferably from 240 to 300° C., particularly preferably from 260 to 290° C.

The pressure in the reaction system is a pressure such that water in the reaction system at the above temperature becomes subcritical water, and is set to be at least the vapor pressure of water at the above temperature. The pressure in the reaction system is, at the above temperature, preferably at least 1.5 MPa (gauge pressure), more preferably at least 3.3 MPa (gauge pressure), particularly preferably at least 4.6 MPa (gauge pressure). The upper limit value is preferably at most 20 MPa (gauge pressure), more preferably at most 15 MPa (gauge pressure), particularly preferably at most 12 MPa (gauge pressure), in view of handling of a high pressure gas.

The time over which the organic compound having a fluorosulfonyl group and subcritical water are contacted can be properly determined depending upon the amount of the organic compound having a fluorosulfonyl group, the content of the fluorosulfonyl group, the temperature, the pressure, etc.

In the reaction of converting the fluorosulfonyl group into a sulfo group, as the case requires, a gas containing molecular oxygen or a gas to maintain the pressure in the reaction system to be a predetermined pressure may be present in the reaction system. The gas is preferably an inert gas (such as rare gas or nitrogen gas), particularly preferably an argon gas, with a view to suppressing decomposition of the organic compound having a fluorosulfonyl group, except for the conversion of the fluorosulfonyl group into a sulfo group.

In the reaction system, as the case requires, a gas containing molecular oxygen may be present. When a gas containing molecular oxygen is present, a non-perfluoro organic compound (such as hydrocarbon) present as an impurity can efficiently be decomposed, whereby the purity of the aimed organic compound having a sulfo group can be increased. Such a method is particularly useful when a high purity perfluorocompound having a sulfo group is to be obtained from a perfluorocompound having a fluorosulfonyl group.

The gas containing molecular oxygen may be pure oxygen gas, may be the air or may be a mixed gas of an oxygen gas with an inert gas.

The reaction container to be used for the above reaction is one which withstands the pressure and temperature conditions in the above reaction and subcritical water. In a case where hydrogen fluoride is to be formed by the reaction of the organic compound having a fluorosulfonyl group with subcritical water, the reaction container is preferably one which withstands hydrofluoric acid.

The material of the reaction container may, for example, be stainless steel, hastelloy or inconel. In a case where hydrogen fluoride is to be formed, hastelloy or inconel is preferred. Otherwise, it is preferred to cover the surface of the reaction container to be in contact with hydrofluoric acid with a material which withstands hydrofluoric acid e.g. by plating or coating. The material which withstands hydrofluoric acid may, for example, be gold.

The stirring means may be a known stirring means such as a magnetic stirrer or a stirring machine provided with a stirring blade. In a case where hydrogen fluoride is to be formed by the reaction of the organic compound having a fluorosulfonyl group with subcritical water, the portion to be in contact with hydrofluoric acid is preferably made of a material which withstands hydrofluoric acid.

In the method for producing an organic compound having a sulfo group of the present invention, the organic compound having a sulfo group is obtained in a state of a liquid composition containing the organic compound having a sulfo group and water. The organic compound having a sulfo group may be used in a state of a liquid composition or may be used after recovered from the liquid composition.

The organic compound having a sulfo group obtained by the method for producing an organic compound having a sulfo group of the present invention is preferably an organic compound having the same molecular structure as the organic compound having a fluorosulfonyl group except for the difference between the sulfo group and the fluorosulfonyl group. However, in the production method of the present invention, usually, a change in the molecular structure occurs to a certain extent. For example, in a case where the organic compound is a fluorinated polymer, an obtainable fluorinated polymer having sulfo groups tends to be a fluorinated polymer having a low molecular weight as compared with the fluorinated polymer having fluorosulfonyl groups as the raw material.

If the fluorinated polymer having sulfo groups obtained by the production method of the present invention has a too low molecular weight as compared with the fluorinated polymer as the raw material, its usefulness, etc. may be impaired. Accordingly, the mass average molecular weight (Mw) of the obtainable fluorinated polymer having sulfo groups is preferably higher than $\frac{1}{5}$ of the mass average molecular weight (Mw) of the fluorinated polymer having fluorosulfonyl groups as the raw material, more preferably higher than $\frac{1}{3}$, particularly preferably higher than $\frac{1}{2}$.

To carry out the production method of the present invention, preferably the following steps are carried out. Specifically, a method comprising the following steps (i) to (iii) in order may be mentioned. As the case requires, the following step (iv) may be carried out to isolate the organic compound having a sulfo group. The following step (iii) is a step to carry out the production method of the present invention.

(i) A step of putting water and an organic compound having a fluorosulfonyl group in a reaction container.

(ii) A step of introducing a gas into the reaction container as the case requires.

(iii) A step of bringing the organic compound having a fluorosulfonyl group into contact with subcritical water under pressure and temperature conditions that water in the reaction container becomes subcritical water, to convert the fluorosulfonyl group into a sulfo group.

(iv) A step of isolating, from a liquid composition containing an organic compound having a sulfo group and water, the organic compound having a sulfo group.

(Step (i))

The step (i) is a step of putting water and an organic compound having a fluorosulfonyl group in a reaction container. Water and the organic compound having a fluorosulfonyl group may be mixed by a stirring means.

In the step (i), before or after water and the organic compound having a fluorosulfonyl group are put in the reaction container, the reaction container may be deaerated, and a desired gas may be introduced after deaeration.

(Step (ii))

The step (ii) is a step of introducing a gas into the reaction container as the case requires. The gas may be introduced continuously or intermittently. In the step (ii), the pressure is not particularly limited so long as water is in a state of subcritical water at the temperature in the step (iii), however, in a case where the gas is introduced at room temperature, it is convenient to adjust the pressure in the reaction container after introduction of the gas to be from 0.01 to 1 MPa (gauge pressure).

[Method for Producing Liquid Composition]

The method for producing a liquid composition of the present invention is a method for producing a liquid composition containing an organic compound having a sulfo group and water, and is a method which comprises treating a composition containing an organic compound having a fluorosulfonyl group and water at from 200 to 320° C. under conditions that water becomes subcritical water, to convert the fluorosulfonyl group into a sulfo group to obtain a composition containing an organic compound having a sulfo group and water.

The content of the organic compound having a fluorosulfonyl group in the composition containing the organic compound having a fluorosulfonyl group and water is preferably from 0.1 to 100 parts by mass, more preferably from 1 to 70 parts by mass, particularly preferably from 3 to 45 parts by mass per 100 parts by mass of water, in view of usefulness of an obtainable liquid composition.

In the above method for producing an organic compound having a sulfo group, the organic compound having a sulfo group is obtained in a state of a liquid composition containing the organic compound having a sulfo group and water. The obtained liquid composition may be used as it is. Accordingly, the present invention also provides the method for producing such a liquid composition.

As the method for producing a liquid composition of the present invention, specifically, a method for carrying out the above-described steps (i) to (iii) in order may be mentioned.

The details of the steps (i) to (iii) are as described above.

The liquid composition contains an organic compound having a sulfo group and water. The organic compound having a sulfo group may be dispersed in water or may be dissolved in water.

The liquid composition, particularly a liquid composition obtained by contact with subcritical water in the presence of a gas containing molecular oxygen, has high purity of the desired organic compound having a sulfo group and can be used as it is, since impurities are decomposed by the contact with subcritical water. In a case where the organic compound having a sulfo group is a perfluoropolymer, it can be used as it is without treatment with hydrogen peroxide solution or the like, as a material for forming an electrolyte membrane or a catalyst layer for a polymer electrolyte fuel cell.

[Method for Hydrolyzing Organic Compound Having Fluorosulfonyl Group]

The method for hydrolyzing an organic compound having a fluorosulfonyl group of the present invention is a method which comprises bringing an organic compound having a fluorosulfonyl group into contact with subcritical water at from 200 to 320° C. to hydrolyze the fluorosulfonyl group. By the hydrolysis method of the present invention, the fluorosulfonyl group of the organic compound is usually converted into a sulfo group by hydrolysis, but the method of the present invention is not limited thereto.

To carry out the hydrolysis method of the present invention, preferably the following steps are carried out.

Specifically, a method of carrying out the following steps (i) to (iii-2) in order may be mentioned.

The following step (iii-2) is a step to carry out the hydrolysis method of the present invention.

(i) A step of putting water and an organic compound having a fluorosulfonyl group in a reaction container.

(ii) A step of introducing a gas into the reaction container as the case requires.

(iii-2) A step of bringing the organic compound having a fluorosulfonyl group into contact with subcritical water under pressure and temperature conditions that water in the reaction container becomes subcritical water to hydrolyze the fluorosulfonyl group.

[Advantageous Effects]

According to the above-described method for producing an organic compound having a sulfo group, method for producing a liquid composition and method for hydrolyzing an organic compound having a fluorosulfonyl group of the present invention, since the fluorosulfonyl group is directly converted into a sulfo group by bringing the compound having a fluorosulfonyl group into contact with subcritical water, the number of steps is small as compared with a conventional method. Further, it is not necessary to use an alkali or an acid, and washing with water is unnecessary, and accordingly the quantity of waste liquid is small as compared with a conventional method. Further, in a case where the compound having a fluorosulfonyl group is brought into contact with subcritical water, the organic compound having a fluorosulfonyl group can efficiently be hydrolyzed, and an organic compound having a sulfo group and a liquid composition can efficiently be produced.

EXAMPLES

Now, the present invention will be described in further detail with reference to Examples. However, present invention is by no means restricted thereto.

Example 1 is a Reference Example, Examples 2 to 6 are Examples of the present invention, and Example 7 is a Comparative Example.

Compounds used in Examples are as follows.

Compound 1 (1,1,2,2-tetrafluoro-2-(1,1,1,2,3,3-hexafluoro-3-(1,2,2-trifluorovinyloxy)propoxy)ethanesulfonyl fluoride):

$CF_2=CFOCF_2CF(CF_3)OCF_2CF_2SO_2F$

Compound 2 (tetrafluoroethylene): $CF_2=CF_2$

Compound 3 (azobisisobutyronitrile):

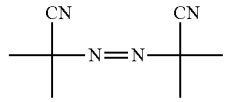

Compound 4 (1,3-dichloro-1,1,2,2,3-pentafluoropropane): $CClF_2CF_2CHClF$

Compound 5 (1,1-dichloro-1-fluoroehtane): $CH_3CCl_2F$

Preparation Example 1

Preparation of Perfluoropolymer Having Fluorosulfonyl Groups

Into a deaerated stainless steel autoclave, 100 parts by mass of compound 1, 28.5 parts by mass of compound 4 as a solvent and 0.0514 part by mass of compound 3 as an initiator were charged. Then, the temperature was increased to 70° C., compound 2 was introduced into the system, and the pressure was maintained at a gauge pressure of 1.14 MPa. Compound 2 was continuously added so that the pressure would be constant at a gauge pressure of 1.14 MPa. 8 Hours later, the autoclave was cooled, compound 2 remaining in the system was purged to terminate the reaction. The obtained liquid composition containing perfluoropolymer (1) was diluted with compound 4, and then compound 5 was added to agglomerate perfluoropolymer (1). After washing with compound 4 and compound 5 and drying, 20 parts by mass of perfluoropolymer (1) having fluorosulfonyl groups was obtained.

$T_Q$ of perfluoropolymer (1) measured by flow tester CFT-500D (manufactured by Shimadzu Corporation) was 230° C.

The content of fluorosulfonyl groups of perfluoropolymer (1) obtained by titration was 1.10 mmol/g.

As calculated from the content of fluorosulfonyl groups of perfluoropolymer (1), perfluoropolymer (1) was a polymer containing units derived from compound 1 and units derived from compound 2 in a molar ratio of 17.8:82.2.

The infrared absorption spectrum of perfluoropolymer (1) was measured as follows. The infrared absorption spectrum is shown in FIG. 1. A peak attributable to a fluorosulfonyl group in the vicinity of 1,470 cm$^{-1}$ was confirmed. Further, a peak attributable to a sulfo group in the vicinity of 1,060 cm$^{-1}$ was not observed.

<Measurement of Infrared Absorption Spectrum>

Particles of perfluoropolymer (1) were pushed against the diamond surface of an accessory (Smart iTR) of single reflection horizontal ATR of a Fourier transform infrared spectrophotometer (Nicolet 380, manufactured by Thermo Fisher Scientific K.K.), and an infrared absorption spectrum was measured.

Example 1

(Step (i))

A beaker made of gold in which 30 mg of perfluoropolymer (1) was put, an Erlenmeyer flask in which deionized water was put and a stainless steel autoclave having an internal capacity of 31 mL were put in a glove bag, and the system in the glove bag was replaced with an argon gas. The deionized water was bubbled with an argon gas, and 10 mL of the deionized water was poured into the beaker made of gold. Then, the beaker made of gold was fixed in the autoclave, the valve was closed to seal the autoclave, and the autoclave was taken out from the glove bag.

(Step (ii))

An argon gas was introduced into the autoclave until the pressure in the autoclave became 0.5 MPa (gauge pressure).

(Step (iii))

The autoclave was heated in an oil bath over a period of 1 hour until the temperature in the autoclave reached 330° C., to convert water in the autoclave into subcritical water, and the autoclave was maintained at this temperature for 6 hours. Then, the autoclave was cooled to room temperature and opened, whereupon a colorless and transparent uniform liquid composition containing perfluoropolymer (2) having sulfo groups was obtained.

The mass average molecular weight of perfluoropolymer (2) was measured as follows. The results are shown in Table 1.

Figure 2:
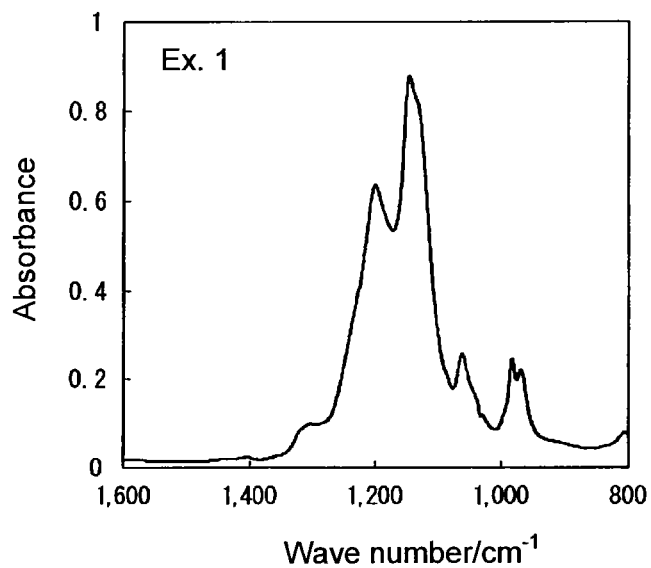
FIG. 2 is an infrared absorption spectrum of perfluoropolymer (2) in Example 1.

The infrared absorption spectrum of perfluoropolymer (2) was measured as follows. The infrared absorption spectrum is shown in FIG. 2. The IR absorbance ratio ($-SO_2F/-SO_3H$) is shown in Table 1. A peak attributable to a sulfo group in the vicinity of 1,060 cm$^{-1}$ was confirmed. A decrease of the peak attributable to a fluorosulfonyl group in the vicinity of 1,470 cm$^{-1}$ was confirmed.

The fluoride ion concentration in the liquid composition was measured as follows. The results are shown in Table 1.
<Measurement of Mass Average Molecular Weight>

To measure the mass average molecular weight of perfluoropolymer (2), the obtained liquid composition was used as it was. By means of size exclusion gas chromatography (SEC), the mass average molecular weight as calculated as polyethylene oxide was obtained.

Apparatus: 8320GPC, manufactured by Tosoh Corporation

Column: α-M and α-3000, manufactured by Tosoh Corporation

Mobile phase: 10 mM di-n-butylammonium acetate (DBAA)-added methanol (for HPLC)

Flow rate: 1.0 mL/min

Oven temperature: 37° C.

System temperature: 37° C.

Amount injected: 50 µL

Detector: Evaporative light scattering detector (ELSD)
<Measurement of Infrared Absorption Spectrum>

The liquid composition was applied to the diamond surface of a single reflection horizontal ATR accessory (universal ATR accessory) of a Fourier transform infrared spectrophotometer (Perkin Elmer Spectrum 100 manufactured by Perkin Elmer) and dried with nitrogen gas, and then an infrared absorption spectrum was measured. The ratio of the absorbance of a peak attributable to a fluorosulfonyl group in the vicinity of 1,470 cm$^{-1}$ to the absorbance of a peak attributable to a sulfo group in the vicinity of 1,060 cm$^{-1}$ (IR absorbance ratio ($-SO_2F/-SO_3H$)) was calculated.
<Measurement of Fluoride Ion Concentration>

The concentration of fluoride ions in the liquid composition was measured by ion chromatography.

Mobile phase: $Na_2B_4O_7$ (6 mM), $H_3BO_3$ (15 mM), $NaHCO_3$ (0.2 mM)

Analysis column: TSKgel Super IC-Anion manufactured by Tosoh Corporation

Mobile phase flow rate: 0.8 mL/min

Column temperature: 40° C.

Detector: conductivity detector provided with suppressor

The theoretical amount of fluoride ions to be formed by hydrolysis of fluorosulfonyl groups in perfluoropolymer (1) is 33 µmol/30 mg polymer.

Example 2

Figure 3:
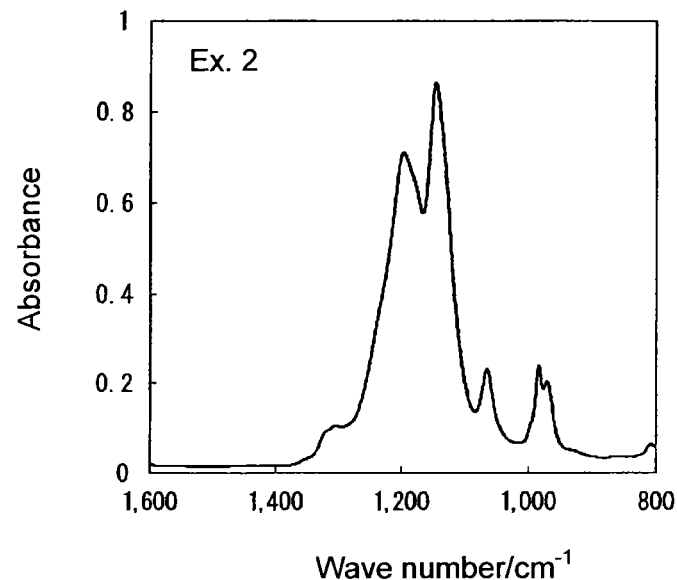
FIG. 3 is an infrared absorption spectrum of perfluoropolymer (3) in Example 2.

A colorless and transparent uniform liquid composition containing perfluoropolymer (3) was obtained in the same manner as in Example 1 except that the temperature in the step (iii) was changed to 300° C. In the same manner as in Example 1, the mass average molecular weight, the infrared absorption spectrum and the fluoride ion concentration were measured. The results are shown in Table 1. The infrared absorption spectrum is shown in FIG. 3. A peak attributable to a sulfo group in the vicinity of 1,060 cm$^{-1}$ was confirmed. A decrease of the peak attributable to a fluorosulfonyl group in the vicinity of 1,470 cm$^{-1}$ was confirmed.

Example 3

Figure 4:
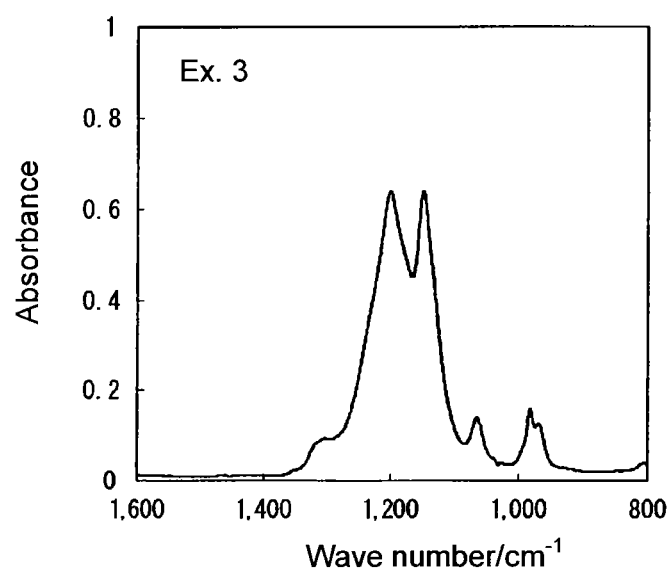
FIG. 4 is an infrared absorption spectrum of perfluoropolymer (4) in Example 3.

A colorless and transparent uniform liquid composition containing perfluoropolymer (4) was obtained in the same manner as in Example 1 except that the temperature in the step (iii) was changed to 290° C. In the same manner as in Example 1, the mass average molecular weight, the infrared absorption spectrum and the fluoride ion concentration were measured. The results are shown in Table 1. The infrared absorption spectrum is shown in FIG. 4. A peak attributable to a sulfo group in the vicinity of 1,060 cm$^{-1}$ was confirmed. A decrease of the peak attributable to a fluorosulfonyl group in the vicinity of 1,470 cm$^{-1}$ was confirmed.

Example 4

Figure 5:
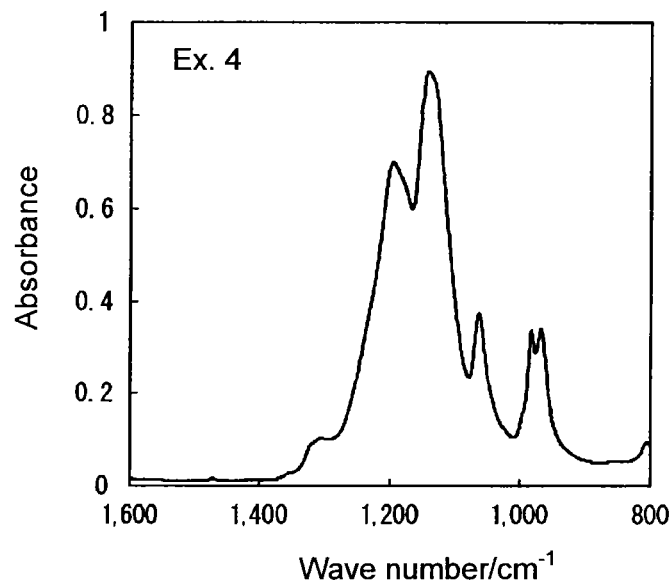
FIG. 5 is an infrared absorption spectrum of perfluoropolymer (5) in Example 4.

A colorless and transparent uniform liquid composition containing perfluoropolymer (5) was obtained in the same manner as in Example 3 except that the amount of perfluoropolymer (1) in the step (i) was changed to 300 mg. In the same manner as in Example 1, the mass average molecular weight, the infrared absorption spectrum and the fluoride ion concentration were measured. Measurement of the mass average molecular weight was carried out after the liquid composition was diluted 10-fold with water. The results are shown in Table 1. The infrared absorption spectrum is shown in FIG. 5. A peak attributable to a sulfo group in the vicinity of 1,060 cm$^{-1}$ was confirmed. A decrease of the peak attributable to a fluorosulfonyl group in the vicinity of 1,470 cm$^{-1}$ was confirmed.

Example 5

Figure 6:
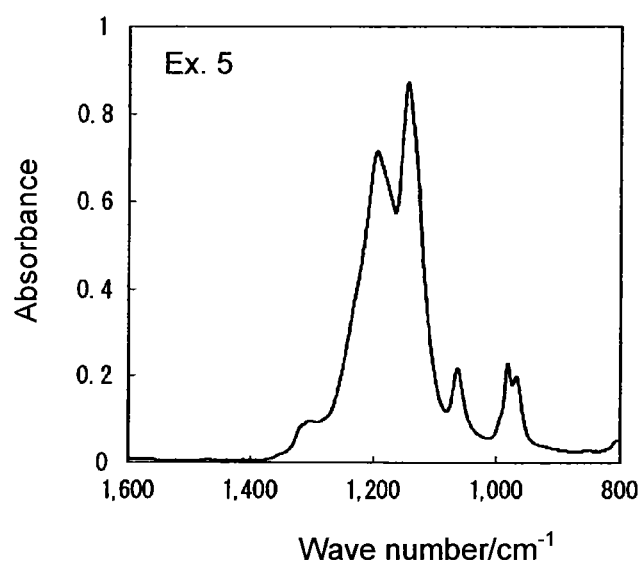
FIG. 6 is an infrared absorption spectrum of perfluoropolymer (6) in Example 5.

A colorless and transparent uniform liquid composition containing perfluoropolymer (6) was obtained in the same manner as in Example 3 except that pure oxygen gas was used instead of argon gas in the step (ii). In the same manner as in Example 1, the mass average molecular weight, the infrared absorption spectrum and the fluoride ion concentration were measured. The results are shown in Table 1. The infrared absorption spectrum is shown in FIG. 6. A peak attributable to a sulfo group in the vicinity of 1,060 cm$^{-1}$ was confirmed. A decrease of the peak attributable to a fluorosulfonyl group in the vicinity of 1,470 cm$^{-1}$ was confirmed.

Example 6

Figure 7:
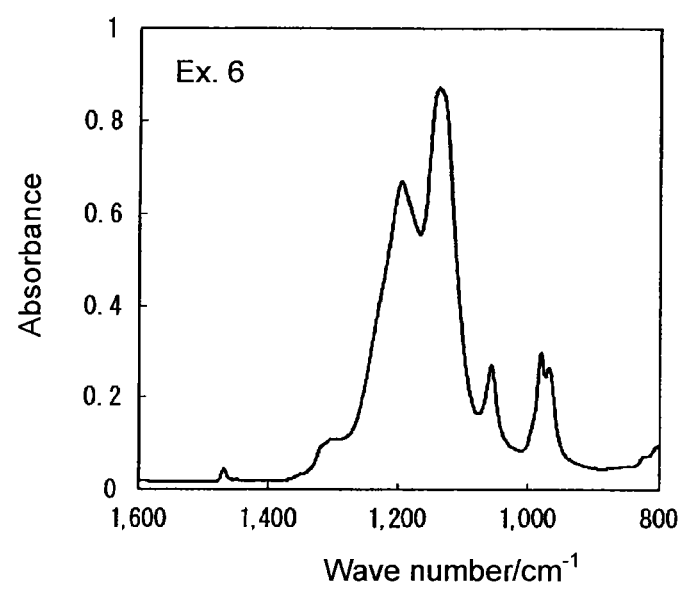
FIG. 7 is an infrared absorption spectrum of perfluoropolymer (7) in Example 6.

A colorless and transparent uniform liquid composition containing perfluoropolymer (7) was obtained in the same manner as in Example 1 except that the temperature in the step (iii) was changed to 280° C. In the same manner as in Example 1, the mass average molecular weight, the infrared absorption spectrum and the fluoride ion concentration were measured. The results are shown in Table 1. The infrared absorption spectrum is shown in FIG. 7. A peak attributable to a sulfo group in the vicinity of 1,060 cm$^{-1}$ was confirmed. A decrease of the peak attributable to a fluorosulfonyl group in the vicinity of 1,470 cm$^{-1}$ was confirmed.

Example 7

Perfluoropolymer (1) was hydrolyzed by being mixed with a potassium hydroxide aqueous solution containing methanol under heating to convert fluorosulfonyl groups to —SO$_3$K groups. The obtained polymer was recovered and washed with water, and then mixed with a sulfuric acid aqueous solution to convert the —SO$_3$K groups to sulfo groups. The obtained polymer was recovered and washed with water to obtain perfluoropolymer (8) having sulfo groups.

Perfluoropolymer (8) was mixed with an ethanol/water mixed solvent (mass ratio: 80/20) so that the concentration of perfluoropolymer (8) became 1 mass %, and the mixture was shaken at 120° C. for 16 hours to obtain a liquid composition containing perfluoropolymer (8).

The liquid composition was diluted with methanol to about 0.3 mass %, and the mass average molecular weight of perfluoropolymer (8) was measured by size exclusion chromatography (SEC), whereupon it was 79,000.

In the production method in each of Examples 2 to 6, fluorosulfonyl groups of perfluoropolymer (1) having fluorosulfonyl groups could efficiently be hydrolyzed, and perfluoropolymers (3) to (7) having sulfo groups and liquid compositions containing such polymers could be produced.

In the production method in Example 1, cleavage of the main chain of the obtained perfluoropolymer (2) having sulfo groups was remarkable.

In the production method in Example 7, the number of steps was large, and the quantity of waste liquid was large.

INDUSTRIAL APPLICABILITY

According to the present invention, from an organic compound having a fluorosulfonyl group, an organic compound having a sulfo group and a liquid composition containing such an organic compound can efficiently be produced. The obtained organic compound having a sulfo group is used as an electrolyte membrane of a polymer electrolyte fuel cell or an ion exchange resin covering catalyst fine particles in a catalyst layer of a polymer electrolyte fuel cell, a humidifying membrane, a dehumidifying membrane or an acid catalyst. After conversion into a lithium salt, it is useful as an electrolyte or an additive for an electrolytic solution of a lithium ion battery.

This application is a continuation of PCT Application No. PCT/JP2012/071872, filed on Aug. 29, 2012, which is based upon and claims the benefit of priority from Japanese Patent Application No. 2011-191547 filed on Sep. 2, 2011 and Japanese Patent Application No. 2012-139964 filed on Jun. 21, 2012. The contents of those applications are incorporated herein by reference in their entireties.

What is claimed is:

1. A method for producing an organic compound having a sulfo group, which comprises bringing an organic compound having a fluorosulfonyl group into contact with subcritical water at from 200 to 320° C. to convert the fluorosulfonyl group into a sulfo group.

2. The method for producing an organic compound having a sulfo group according to claim 1, wherein the organic compound having a fluorosulfonyl group is a perfluorocompound.

3. The method for producing an organic compound having a sulfo group according to claim 1, wherein the organic compound having a fluorosulfonyl group is a fluorinated polymer.

4. A method for producing a liquid composition containing an organic compound having a sulfo group and water, which comprises treating a composition containing an organic compound having a fluorosulfonyl group and water at from 200 to 320° C. under conditions that water becomes subcritical water, to convert the fluorosulfonyl group into a sulfo group to obtain a composition containing an organic compound having a sulfo group and water.

TABLE 1

|  |  |  | Unit | Ex. 1 | Ex. 2 | Ex. 3 | Ex. 4 | Ex. 5 | Ex. 6 | Ex. 7 |
|---|---|---|---|---|---|---|---|---|---|---|
| Production conditions | Step (i) | Amount of perfluoropolymer (1) | [mg] | 30 | 30 | 30 | 300 | 30 | 30 | — |
|  | Step (ii) | Gas in autoclave |  | Argon gas | Argon gas | Argon gas | Argon gas | Pure oxygen gas | Argon gas | — |
|  | Step (iii) | Temperature | [° C.] | 330 | 300 | 290 | 290 | 290 | 280 | — |
| Liquid composition | Perfluoropolymer | Kind |  | (2) | (3) | (4) | (5) | (6) | (7) | (8) |
|  |  | Mass average molecular weight |  | 6,000 | 39,000 | 53,000 | 57,000 | 55,000 | 63,000 | 79,000 |
|  |  | IR absorbance ratio (—SO$_2$F/—SO$_3$H) |  | 0/100 | 1.1/98.9 | 4.4/95.6 | 2.2/97.8 | 1.8/98.2 | 15.7/84.3 | — |
|  |  | Fluoride ion concentration | [μmol/30 mg polymer] | 170 | 44.1 | 45.1 | 31.5 | 39.3 | 29.9 | — |

5. The method for producing a liquid composition according to claim 4, wherein the organic compound having a fluorosulfonyl group is a perfluorocompound.

6. The method for producing a liquid composition according to claim 4, wherein the organic compound having a fluorosulfonyl group is a fluorinated polymer.

7. A method for hydrolyzing an organic compound having a fluorosulfonyl group, which comprises bringing an organic compound having a fluorosulfonyl group into contact with subcritical water at from 200 to 320° C. to hydrolyze the fluorosulfonyl group.

8. The method for hydrolyzing an organic compound having a fluorosulfonyl group according to claim 7, wherein the organic compound having a fluorosulfonyl group is a perfluorocompound.

9. The method for hydrolyzing an organic compound having a fluorosulfonyl group according to claim 7, wherein the organic compound having a fluorosulfonyl group is a fluorinated polymer.

10. The method for hydrolyzing an organic compound having a fluorosulfonyl group according to claim 7, wherein the fluorosulfonyl group is converted into a sulfo group by hydrolysis.

* * * * *